Jan. 12, 1971 R. KORDES Plant Pat. 3,014
ROSE PLANT
Filed Feb. 10, 1969
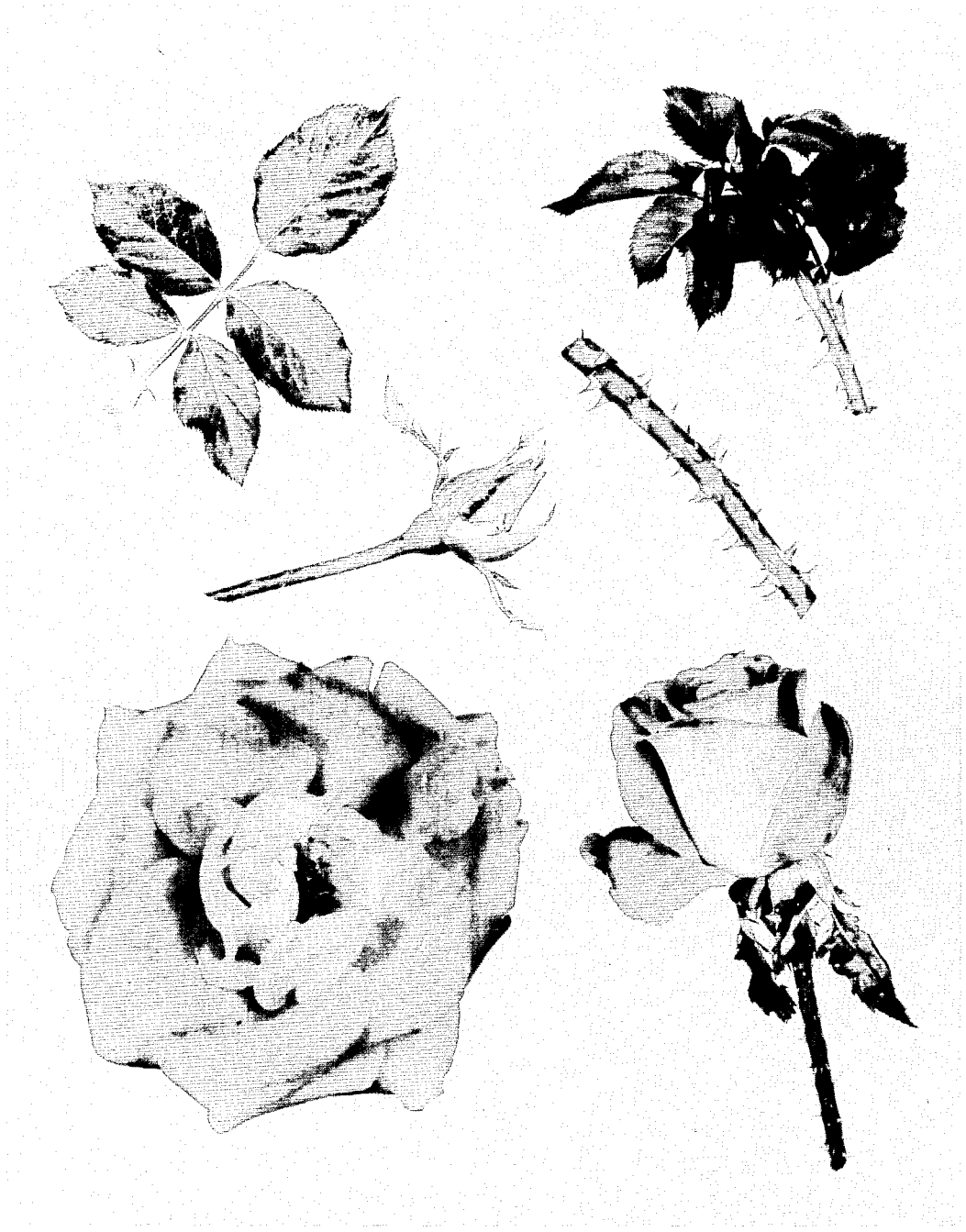
Inventor.
Reimer Kordes
By: Robb & Robb
Attorneys.

United States Patent Office

Plant Pat. 3,014
Patented Jan. 12, 1971

3,014
ROSE PLANT

Reimer Kordes, Barmstedt, near Elmshorn, Germany, assignor to Jackson & Perkins Company, Newark, N.Y., a corporation of New York Filed Feb. 10, 1969, Ser. No. 798,199
Int. Cl. A01h 5/00
U.S. Cl. Plt.—12 1 Claim The present invention relates to a new and distinct variety of rose plant of the hybrid tea class, which was originated by me by crossing an unnamed and unpatented seedling of the rose variety known as "Detroiter" (U.S. Plant Pat. 1,219) × the rose variety known as "Liberty Bell" (unpatented) with an unnamed and unpatented seedling of "Detroiter" × the rose variety known as "Kordes' Perfecta" (U.S. Plant Pat. No. 1,604).

The primary objective of this breeding was to produce a new and improved rose variety of the hybrid tea class which bears large, well-formed, brightly colored flowers on a vigorous and diseases resistant plant. This objective was fully achieved, along with other desirable improvements, as evidenced by the following unique combination of characteristics which are outstanding in the new variety and which distinguish it from its parents, as well as from all other rose varieties of which I am aware:

(1) An upright, vigorous, heavily branched and disease resistant plant habit;

(2) Continuous production of large, wellformed flowers throughout the growing season;

(3) An imbricated open flower form, with the center covered by incurved petals; and (4) A distinctive, attractive and exceptionally brilliant Blood Red color of the open flows, contrasting with the white color on the reverse of the petals.

Asexeual reproduction of the new variety by budding, as performed in Germany and at Wasco, Calif., U.S.A., shows that the foregoing characteristics and distinction come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with Wilson's Horticultural Colour Chart (hereinafter abbreviated as (W)) and Ridgeway's Color Standards and Nomenclature (hereinafter abbreviated as (R)), except where general color terms of ordinary dictionary significance are obvious:

Parentage: Seedling.
- *Seed parent.*—An unnamed seedling of "Detroiter" × "Liberty Bell."
- *Pollen parent.*—An unnamed seedling of "Detroiter" × "Kordes' Perfecta."

Classification:
- *Botanic.*—Rosa.
- *Commercial.*—Hybrid tea.

FLOWER (Observations made from specimens grown at Newark, N.Y., U.S.A., in the afternoon during the middle of the month of September.)

Blooming habit:
- *Recurrent.*—Continuous.

Bud:
- *Size.*—Large.
- *Form.*—Pointed; ovoid.
- *Color.*—When sepals first divide: Cardinal Red, Plate 822, page 168 (W), shaded with Yellow Ochre, Plate 07/2, page 101 (W). When half-blown: Inside of petals—Blood Red, Plate 820, page 166 (W); reverse of petals—Near white, shaded and suffused with from Carmine Rose, Plate 621, page 75 (W) to Carmine Rose, Plate 621/3, page 75 (W).
- *Sepals.*—Smooth edge on 2 sepals; usually branched with foliaceous appendages on 3 sepals. Color: Inside—Fern Green, Plate 0862, page 186 (W); outside—Fern Green, Plate 0862, page 186 (W), covered with whitish tomentum.
- *Receptacle.*—Color: Fern Green, Plate 0862, page 186 (W). Shape: Funnel. Size: Large. Surface: Smooth.
- *Peduncle.*—Length: Medium. Surface: Prickly. Strength: Stiff. Color: Morocco Red, Plate 1, 5k (R).

Bloom:
- *Size.*—Large; from 4 inches to 6 inches.
- *Borne.*—Singly.
- *Stems.*—Medium length; strong.
- *Form (when first open).*—Flat; center petals cover center of flows. Permanence: Retains its form to the end. Petalage: Form approximately 25 to 35 petals under normal conditions.
- *Color.*—Center of flower: Blood Red, Plate 820, page 166 (W). Outer petals: Blood Red, Plate 820, page 166 (W). Inside of petals: Blood Red, Plate 820, page 166 (W). Reverse of petals: Near white, lightly washed with from Carmine Rose, Plate 621, page 75 (W) to Carmine Rose, Plate 621/3, page 75 (W). Base of petals: Small area of Citron Green, Plate 763/2, page 100 (W). General tonality from a distance: Blood Red, Plate 820, page 166 (W), except where near white reverse of petals is visible.
- *Discoloration.*—General tonality at end of first day: Blood Red, Plate 820, page 166 (W). Third day: Slightly darker than Blood Red, Plate 820, page 166 (W).
- *Fragrance.*—Slight. Nature: Fruity.

Petals:
- *Texture.*—Thick.
- *Surface appearance.*—Inside: Velvety. Reverse: Satiny.
- *Form.*—Round.
- *Arrangement.*—Mostly imbricated.
- *Petaloids in center.*—Few.
- *Persistence.*—Drop off cleanly.
- *Lasting quality.*—On the plant: Long. As cut flower: Fair.

REPRODUCTIVE ORGANS

Anthers: Large; regularly arranged around styles.
- *Color.*—Yellow.

Filaments (threads): Medium length.
- *Color.*—Yellow.

Styles: Bunched.

Stigmas:
- *Color.*—White.

Ovaries: All enclosed in calyx.

Fruit: None observed.

PLANT

Form: Bush; well-branched.
Growth: Medium height.
Foliage: Compound of 5 leaflets.
*Size.*—Medium.
*Quantity.*—Normal.
*Color.*—New foliage: Bay, Plate II, 7m (R). Old foliage: Normal green.
*Shape.*—Elliptical.
*Texture.*—Upper side: Smooth. Underside: Smooth.
*Ribs and veins.*—Ordinary.
*Edge.*—Serrated.
*Serration.*—Single.
*Petiole (rachis).*—Color: Green. Underside: Prickly.
*Stipules.*—Short; slightly serrated.
*Disease resistance.*—Normal resistance to mildew and blackspot, as determined by comparison with other rose varieties grown under the same conditions at Newark, N.Y., U.S.A.
Wood:
*New wood.*—Color: Light green. Bark: Smooth.
*Old wood.*—Color: Green. Bark: Smooth.

Thorns:
*Thorns.*—Quantity: On main stalks from base—many; on laterals from stalk—many. Form: Broad base; long; hooked downward. Color (when young): Straw. Position: Irregular.
*Prickles.*—Quantity: On main stalks—few; on laterals—few. Color: Brown.

I claim:

1. A new and distinct variety of rose plant of the hybrid tea class, substantially as herein shown and described, characterized particularly as to novelty by the unique combination of an upright, vigorous, heavily branched and disease resistant plant habit, continuous production of large, well-formed flowers throughout the growing season, an imbricated open flower form, with the center covered by incurved petals, and a distinctive, attractive and exceptionally brilliant Blood Red color of the open flowers, contrasting with the white color on the reverse of the petals.

No references cited.

ROBERT E. BAGWILL, Primary Examiner